United States Patent
Scavone et al.

(10) Patent No.: US 6,495,149 B1
(45) Date of Patent: Dec. 17, 2002

(54) TOPICAL LEAVE-ON COMPOSITIONS CONTAINING SELECTED PANTOTHENIC ACID DERIVATIVES

(75) Inventors: Timothy Alan Scavone, Loveland, OH (US); Benjamin Scott Schlagheck, Mason, OH (US); Lisa Ann Runtz, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/928,295

(22) Filed: Aug. 10, 2001

(51) Int. Cl.$^7$ .............................. A61K 6/00; A61K 7/00; A61K 7/32; A61K 7/34; A61K 7/38; A61K 31/74
(52) U.S. Cl. ..................... 424/401; 424/65; 424/68; 424/66; 424/78.02
(58) Field of Search ................ 424/401, 76.2, 424/76.3, 65, 67, 68, 69

(56) References Cited

U.S. PATENT DOCUMENTS

| | | | |
|---|---|---|---|
| 4,478,853 A | | 10/1984 | Chaussee |
| 4,963,591 A | * | 10/1990 | Fourman ..................... 514/944 |
| 4,970,220 A | | 11/1990 | Chaussee |
| 5,369,092 A | * | 11/1994 | Blakeway et al. ............. 512/2 |
| 5,540,853 A | * | 7/1996 | Trinh et al. .................. 510/101 |
| 5,612,324 A | | 3/1997 | Lin et al. |
| 5,710,141 A | | 1/1998 | Lin et al. |
| 5,750,122 A | | 5/1998 | Evans et al. |
| 5,824,666 A | | 10/1998 | Deckner et al. |
| 5,827,508 A | | 10/1998 | Tanner et al. |
| 5,871,754 A | | 2/1999 | Briggs et al. |
| 5,871,760 A | | 2/1999 | Doughty et al. |
| 5,919,439 A | | 7/1999 | Torgerson et al. |
| 5,928,631 A | * | 7/1999 | Lucas et al. ................... 424/65 |
| 5,935,556 A | | 8/1999 | Tanner et al. |
| 5,961,999 A | | 10/1999 | Bimczok et al. |
| 5,989,528 A | | 11/1999 | Tanner et al. |
| 6,086,903 A | | 7/2000 | Trinh et al. |

FOREIGN PATENT DOCUMENTS

| WO | 93/21899 A1 | 11/1993 |
|---|---|---|
| WO | 93/24101 A1 | 12/1993 |

OTHER PUBLICATIONS

"Ethyl Panthenol", Roche product publication.

* cited by examiner

Primary Examiner—Jose' G. Dees
Assistant Examiner—Sharmila S Gollamudi
(74) Attorney, Agent, or Firm—Jack L. Oney; Tara M. Rosnell; Steven W. Miller

(57) ABSTRACT

Disclosed are topical leave-on compositions such as antiperspirant and deodorant compositions comprising (b) from about 0.01% to about 10% by weight of selected pantothenic acid derivatives, (b) from about 10% to about 99.89% by weight of a liquid carrier, wherein the composition has a pH of from about 2.0 to about 5.0, or otherwise comprises an acidic skin active agent or other similar material such as an aluminum-containing antiperspirant active. The selected pantothenic acid derivatives remain stable within the antiperspirant or acidic compositions and provide improved skin feel and cosmetics benefits.

31 Claims, No Drawings

TOPICAL LEAVE-ON COMPOSITIONS CONTAINING SELECTED PANTOTHENIC ACID DERIVATIVES

TECHNICAL FIELD

The present invention relates to topical leave-on compositions, including antiperspirant and deodorant compositions, that contain selected acid-stable pantothenic acid derivatives. The selected materials are soothing to the skin, provide for improved application cosmetics, and remain acid-stable when used in acidic topical compositions or those compositions containing aluminum-containing antiperspirant actives or other acidic skin active materials.

BACKGROUND OF THE INVENTION

Pantothenic acid derivatives such as panthenol and similar other materials are commonly used in a variety of chemical forms and derivatives in personal care products intended for topical application to the hair or skin. These materials are well known for use in a variety of hair care products as well as in topical skin care products to provide a smooth, soothing skin feel, and to provide a soothing application to otherwise irritated skin. These materials have also been described for use in antiperspirant and deodorant products, most often as racemic mixtures of the D and L isomeric forms of panthenol or as the pure, biologically active, D isomeric form.

It has now been found, however, that many pantothenic acid derivatives such as panthenol and similar other materials are unstable when formulated into compositions comprising aluminum-containing antiperspirant actives or other acidic materials including organic acids. It has been found that many pantothenic acid derivatives such as panthenol are relatively unstable when formulated into such compositions, or even when formulated into compositions that otherwise have an acidic pH in the range of from about 2.0 to about 5.0. It has been found that these materials often undergo an acid-catalyzed degradation when used in combination with organic acids or other acidic materials such as aluminum-containing antiperspirant actives, especially when the combination is within an aqueous system, to form by-products that readily and undesirably form off-odors as well as small crystals around and throughout the composition. This degradation can occur during formulation and processing, as well as during prolonged product storage, but is most significant when the formulating, processing, or prolonged storage is accompanied by elevated temperatures.

It has also been found that pantothenic acid derivatives can be formulated into compositions having a pH of from about 2.0 to about 5.0, with little or none of the above-described chemical degradation, crystal formation, and off-odor formation, provided that the pantothenic acid derivative is selected to have the chemical formula as defined herein. It has also been found that pantothenic acid derivatives can now be formulated in combination with acidic materials such as organic acids or aluminum-containing antiperspirant actives, without the above-described off-odor development and crystal formation, provided that the pantothenic acid derivatives are also selected to have the chemical formula as defined herein.

It has also been found that the selected pantothenic acid derivatives as described herein also help to soften or condition underarm hair, or underarm hair and skin, and that this softened or conditioned underarm hair, or underarm hair and skin, is much easier to shave. It is believed that the softened or conditioned underarm hair cuts more easily during the shaving process as a result of less drag on the hair or skin now caused by the shaving device.

It is therefore an object of the present invention to provide a topical leave-on composition having a pH of from about 2.0 to about 5.0, within which a pantothenic acid derivative is formulated and remains more acid-stable over prolonged periods of time. It is a further object of the present invention to provide an antiperspirant and deodorant composition that contains an aluminum-containing antiperspirant active, and which contains a pantothenic aced derivative that remains more acid-stable over prolonged periods of time despite concurrent use of an otherwise acid antiperspirant active such as an aluminum-containing active. It is a further object of the present invention to provide a topical leave-on composition that contains an organic acid and a pantothenic acid derivative, wherein the pantothenic acid derivative is selected so that it remains more acid-stable within the composition over prolonged periods.

It is yet a further object of the present invention to provide a method of softening or conditioning underarm hair, and to provide a method of enhancing ease of shaving of underarm through the softening or conditioning of the underarm hair by the topical application of the pantothenic acid derivatives as described herein.

SUMMARY OF THE INVENTION

The present invention is directed to topical leave-on compositions comprising (b) from about 0.01% to about 10% by weight of selected pantothenic acid derivatives having the formula:

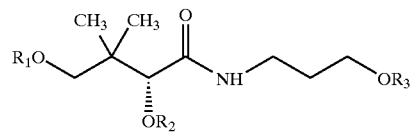

wherein $R_1$, $R_2$ and $R_3$ are independently selected from the group consisting of hydrogen, C2–C20 hydrocarbons, C2–C20 carboxylic acid esters, and combinations thereof, and wherein not more than two of R1, R2 and R3 are hydrogen; and (b) from about 10% to about 99.89% by weight of a liquid carrier, wherein the composition has a pH of from about 2.0 to about 5.0, or otherwise contains an acid material such as an organic acid or an aluminum-containing antiperspirant active.

It has been found that the topical leave-on compositions of the present invention can be formulated to comprise pantothenic acid derivatives that remain more stable in an acidic formulation or within a formulation that otherwise contains organic acids or aluminum-containing antiperspirant actives.

The present invention is also directed to methods of preventing or inhibiting underarm perspiration wetness and odor, and to methods of enhancing the ease of shaving underarm hair by conditioning or softening the underarm hair, or by conditioning the underarm hair and or skin, all through the underarm application of the antiperspirant and deodorant embodiments of the present invention.

DETAILED DESCRIPTION OF THE INVENTION

The topical leave-on compositions of the present invention comprise as essential components selected pantothenic acid derivatives, a liquid carrier, and an acidic profile defined by a formulation pH of from about 2.0 to about 5.0 or an acidic profile defined by the concurrent use of acidic materials such as organic acids or aluminum-containing antiperspirant actives. Each of these essential components or features of the compositions of the present invention is described hereinafter in more detail.

The term "anhydrous" as used herein refers to those compositions or materials that contain less than about 15%, more preferably less than about 10%, even more preferably less than about 1%, most preferably zero percent, by weight of water.

The term "ambient conditions" as used herein refers to surrounding conditions under about one (1) atmosphere of pressure, at about 50% relative humidity, and at about 25° C., unless otherwise specified. All values, amounts and measurements described herein are obtained under ambient conditions unless otherwise specified.

The term "volatile" as used herein refers to those materials that have a measurable vapor pressure at 25° C. Such vapor pressures will typically range from about 0.01 mmHg to about 6 mmHg, more typically from about 0.02 mmHg to about 1.5 mmHg, and have an average boiling point at one (1) atmosphere of pressure (atm) of less than about 250° C., more typically less than about 235° C. at one (1) atm. Conversely, the term "non volatile" refers to those materials that are not "volatile" as defined herein.

The term "leave-on" as used herein refers to the compositions of the present invention and means that such compositions are intended solely for leave-on application to the skin, and therefore specifically excludes rinse-off applications such as shampoos, facial or hand cleansers, or any body wash or cleanser composition. In this context, the topical leave-on compositions of the present invention are preferably substantially free of cleansing surfactants, which means that the leave-on compositions preferably contain less than 1% by weight of such cleansing surfactants, even more preferably less than 0.5% by weight of such cleansing surfactants, most preferably zero percent by weight of such cleansing surfactants. The compositions may, however, contain emulsifying or other processing surfactants that are not intended to provided any significant cleansing benefits when applied topically to the skin.

The topical leave-on compositions of the present invention, including the antiperspirant and deodorant embodiments thereof, can comprise, consist of, or consist essentially of the essential elements and limitations of the invention described herein, as well as any additional or optional ingredients, components, or limitations known or otherwise effective for use in such compositions.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Antiperspirant Active

The antiperspirant and deodorant embodiments of the present invention comprise an aluminum-containing antiperspirant active suitable for application to human skin. The concentration of the active should be sufficient to provide the desired perspiration wetness or odor control from the formulation selected.

The antiperspirant active concentration in the antiperspirant and deodorant embodiments of the present invention ranges from about 0.1% to about 30%, more preferably from about 5% to about 30%, by weight of the composition. These weight percentages are calculated on an anhydrous metal salt basis exclusive of water and any complexing agents such as glycine, glycine salts, or other complexing agents. The antiperspirant active can be solubilized or solid, but is preferably in the form of a dispersed solid particulate. The dispersed particulates most typically have average particle size or diameter of less than about 100 µm, more typically from about 1 µm to about 40 µm.

The antiperspirant active for use in the antiperspirant and deodorant embodiments of the present invention include any aluminum-containing material having antiperspirant activity, which can be used alone or in combination with other antiperspirant active materials such as zirconium-containing actives. The antiperspirant actives suitable for use herein include astringent metallic salts, especially inorganic and organic salts of aluminum, zirconium and zinc, as well as mixtures thereof. Particularly preferred are aluminum-containing and/or aluminum/zirconium-containing salts or materials, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant and deodorant embodiments of the present invention include those that conform to the formula:

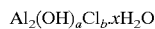

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant and deodorant embodiments of the present invention include those which conform to the formula:

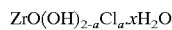

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

Antiperspirant actives suitable for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

It has been found that aluminum-containing actives when used in combination with panthenol, pantothenic acid derivatives, and other similar materials, promotes the acid degradation of the panthenol material during processing and prolonged storage, especially when such processing or prolonged storage is at elevated temperatures. The degradation results in undesirable crystal formation and off-odor development. It has also been found that this acid degradation and subsequent crystal formation and off-odor development can be minimized or avoided by selection of the pantothenic acid derivatives as defined herein.

Organic Acids

The topical leave-on compositions of the present invention include aqueous compositions containing organic acids, wherein the organic acid preferably helps to maintain the composition pH from about 2.0 to about 5.0, more preferably from about 3.0 to about 4.5.

It has been found that the selected pantothenic acid derivatives as defined herein are more stable than many other panthenol-related materials as formulated in an aqueous system containing an organic acid, or even as formulated into an anhydrous system containing at least small amounts of water as the term anhydrous is defined herein. In this context, the term "aqueous" refers to those embodiments of the present invention that contain at least 15%, preferably from about 30% to about 99%, of water by weight of the composition.

Non limiting examples of organic acids suitable for use in the topical leave-on compositions of the present invention include salicylic acid, lactic acid, glycolic acid, 3-hydroxy benzoic acid, 4-hydroxy benzoic acid, acetyl salicylic acid, 2-hydroxybutanoic acid, 2-hydroxypentanoic acid, 2-hydroxybutanoic acid, cis-retinoic acid, trans-retinoic acid, azelaic acid, lactic acid, glycolic acid, pyruvic acid, and combinations thereof. Highly preferred is salicylic acid. Salicylic acid and other suitable organic acids are described in U.S. Pat. No. 5,710,141 (Lin et al.), which description is incorporated herein by reference.

The organic acid concentration in the topical leave-on compositions of the present invention, especially the salicylic acid-containing embodiments, preferably represent from about 0.01% to about 20%, more preferably from about 0.10% to about 7.0%, even more preferably from about 0.5% to about 2.0%, of such organic acid, especially salicylic acid, by weight of the composition.

Pantothenic Acid Derivatives

The topical leave-on compositions of the present invention, including the antiperspirant and deodorant embodiments thereof, comprise selected pantothenic acid derivatives that remain more stable than panthenol and other similar materials in acidic compositions or in compositions containing acid-producing materials such as aluminum-containing actives, and are also suitable for topical leave-on application to the skin. The selected pantothenic acid derivatives are most typically in liquid form and dispersed throughout or otherwise solubilized within the liquid carrier component of the composition.

The term "pantothenic acid derivative" as used herein refers to those materials that conform to the formula:

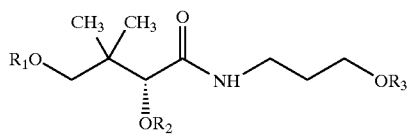

wherein $R_1$, $R_2$ and $R_3$ are hydrogen, C2–C20 hydrocarbons, C2–C20 carboxylic acid esters, or combinations thereof, provided that not more than two of R1, R2 and R3 are hydrogen. Preferably, $R_1$, $R_2$ and $R_3$ are independently selected from hydrogen, C2–C8 hydrocarbons, C2–C8 carboxylic acid esters, or combinations thereof; more preferably, $R_1$ and $R_2$ are hydrogen, and $R_3$ is a C2–C8 hydrocarbon, C2–C8 carboxylic acid ester, or combinations thereof; most preferably, $R_1$ and $R_2$ are hydrogen and $R_3$ is ethyl. The selected pantothenic acid derivatives may be derived or otherwise obtained from any known source, which may include pantothenic acid or materials other than pantothenic acid, so long as the resulting material has the above defined chemical formula.

Specific non-limiting examples of selected pantothenic acid derivatives for use herein include ethyl panthenol, panthenyl triacetate, and combinations thereof. Preferred are the d-isomeric forms of such derivative forms, most preferably d-ethyl panthenol.

The concentration of the pantothenic acid derivative for use in the compositions of the present invention preferably ranges from about 0.01% to about 10%, more preferably from about 0.05% to about 5.0%, even more preferably from about 0.5% to about 3.0%, by weight of the composition.

Liquid Carrier

The topical leave-on compositions of the present invention, including the antiperspirant and deodorant embodiments thereof, comprise a liquid carrier at concentrations ranging from about 10% to about 99.89%, preferably from about 20% to about 70%, by weight of the composition. Such concentrations will vary depending upon variables such as product form, desired product hardness, selection of other ingredients in the composition, and so forth. The liquid carrier for use in the composition can be aqueous or anhydrous, and includes any liquid material, or any non-liquid material that is otherwise rendered liquid within the composition, that is known for use in personal care applications or is otherwise suitable for topical application to the skin.

The topical leave-on compositions of the present invention, including the antiperspirant and deodorant embodiments thereof, may be aqueous or anhydrous as defined herein, but either way, will most typically comprise at least small amounts of water, typically as water of hydration from formulated solids such as antiperspirant active salts. For aqueous embodiments of the compositions of the present invention, the liquid carrier is an aqueous carrier comprising from about 15% to about 99%, more preferably from about 30% to about 99%, water by weight of the composition, wherein the aqueous carrier or the topical leave-on composition preferably has a pH of from about 2.0 to about 5.0, more preferably from about 3 to about 4.5.

The liquid carrier component of the compositions of the present invention may comprise a volatile silicone liquid, which may include cyclic, linear and/or branched chain silicones. The concentration of volatile silicones in the topical leave-on compositions as well as the antiperspirant and deodorant embodiments thereof preferably ranges from about 5% to about 80%, preferably from about 20% to about 60%, more preferably from about 30% to about 60%, by weight of the composition. The volatile silicone is preferably a cyclic silicone having from about 3 to about 7, more preferably from about 5 to about 6, silicon atoms. Most preferred are those that conform to the formula:

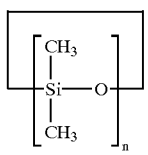

wherein n is from about 3 to about 7, preferably from about 5 to about 6, most preferably 5. These volatile cyclic silicones generally have a viscosity of less than about 10 centistokes. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). Non limiting examples of suitable volatile silicones are described in Todd et al., "Volatile Silicone Fluids for Cosmetics", Cosmetics and Toiletries, 91:27–32 (1976), which descriptions are incorporated herein by reference.

The carrier liquid for use in the topical leave-on compositions may comprise a non-volatile silicone liquid, preferred concentrations of which range from about 1% to about 35%, more preferably from about 5% to about 30%, by weight of the composition. The non volatile silicone carrier is preferably a liquid at or below human skin temperature, or otherwise in liquid form within the topical leave-on composition during or shortly after topical application. Preferred are those nonvolatile liquid silicones that conform to either of the formulas:

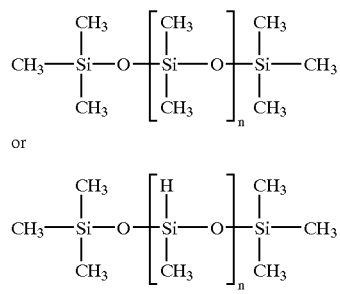

wherein n is sufficiently large to provide a viscosity of up to about 100,000 centistokes, preferably less than about 500 centistoke, more preferably from 10 centistoke to about 200 centistoke, even more preferably from 10 centistoke to about 50 centistoke, as measured under ambient conditions. Specific non limiting examples of suitable non volatile, linear, silicone carriers include Dow Corning 200, hexamethyldisiloxane, Dow Corning 225, Down Corning 1732, Dow Corning 5732, Dow Corning 5750 (available from Dow Corning Corp.); and SF-96, SF-1066 and SF18 (350) Silicone Fluids (available from G.E. Silicones).

Many other liquid carriers known for use in personal care products can be used in the topical leave-on compositions of the present invention, alone or in combination with the liquid carriers described in more detail herein. Examples of such other carrier liquids are disclosed in U.S. Pat. No. 6,013,248 (Luebbe et al.) and U.S. Pat. No. 5,968,489 (Swaile et al.), which descriptions are incorporated herein by reference.

Suspending Agents

The topical leave-on compositions of the present invention, including the antiperspirant and deodorant embodiments thereof, may further comprise a suspending or thickening agent to help provide the compositions with the desired viscosity, rheology, texture and/or product hardness, or to otherwise help suspend any dispersed solids or liquids within the composition.

The term "suspending agent" as used herein, unless otherwise specified, means any material known or otherwise effective in providing suspending, gelling, viscosifying, solidifying and/or thickening properties to the composition or which otherwise provide structure to the final product form. These suspending agents include gelling agents, and polymeric or nonpolymeric or inorganic thickening or viscosifying agents. Such materials will typically be solids under ambient conditions and include organic solids, silicone solids, crystalline or other gellants, inorganic particulates such as clays or silicas, or combinations thereof.

The concentration and type of suspending agent selected for use in the topical leave-on compositions of the present invention will vary depending upon the desired product hardness, rheology, and/or other related product characteristics. For most suspending agents suitable for use herein, total concentrations range from about 0.1% to about 40%, more typically from about 0.1% to about 35%, by weight of the composition. Suspending agent concentrations will tend to be lower for liquid embodiments (e.g., pressurized or other liquid sprays, roll-ons, etc) and higher for semi-solid (e.g., soft solids or creams) or solid stick embodiments.

Non limiting examples of suitable suspending agents include hydrogenated castor oil (e.g., Castor wax MP80, Castor Wax, etc.), fatty alcohols (e.g., stearyl alcohol), solid paraffins, triglycerides and other similar solid suspending esters or other microcrystalline waxes, silicone and modified silicone waxes. Non limiting examples of optional suspending agents suitable for use herein are described in U.S. Pat. No. 5,976,514 (Guskey et al.), U.S. Pat. No. 5,891,424 (Bretzler et al.), which descriptions are incorporated herein by reference.

Other suitable suspending agents include silicone elastomers at concentrations ranging from about 0.1% to about 10%, by weight of the composition. Non-limiting examples of such silicone elastomer materials suitable for use as a suspending agent herein are described in U.S. Pat. No. 5,654,362 (Schulz, Jr. et al.); U.S. Pat. No. 6,060,546 (Powell et al.) and U.S. Pat. No. 5,919,437 (Lee et al.), which descriptions are incorporated herein by reference. These silicone elastomers materials can also be added for their skin feel or other cosmetic benefits alone, or for such benefits in combination with suspending agent benefits.

Optional Ingredients

The topical leave-on compositions of the present invention, including the antiperspirant and deodorant embodiments thereof, may further comprise any acid-stable optional ingredient that is known for or otherwise suitable for use in topical or personal care products, including antiperspirant and deodorant compositions.

Non limiting examples of optional ingredients include dyes or colorants, emulsifiers, perfumes, propellants, antimicrobial deodorants, deodorant perfumes, preservatives, vitamins, non-vitamin nutrients, emollients, coupling agents or other solvents, processing aides such as viscosity modifiers, and so forth. Examples of such optional materials, especially for use in the antiperspirant and deodorant embodiments of the present invention, are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference. Other examples of optional materials for use in the topical leave-on compositions of the present invention are described in U.S. Pat. No. 5,824,666 (Deckner et al.) and U.S. Pat. No. 5,710,141 (Lin et al.), which descriptions are incorporated herein by reference.

Still other optional materials include topical substrates on or within which the composition of the present invention is coated, impregnated, or otherwise associated. Suitable substrates include any woven or non-woven, water-soluble or insoluble, substrate that is known for or otherwise suitable for topical application to the skin, and which is compatible with the selected ingredients in the composition. Non-limiting examples of some suitable substrates for use herein are described in U.S. Ser. No. 09/624,320 (Pung et al.), filed Jul. 24, 2000, which description is incorporated herein by reference.

Methods of Manufacture

The topical leave-on compositions of the present invention, including the antiperspirant and deodorant embodiments thereof, may be prepared by any known or otherwise effective technique suitable for formulating the desired topical or antiperspirant/deodorant product form.

Suitable methods of making various antiperspirant and deodorant products forms are described at length in the antiperspirant and deodorant art. These various methods can easily be used or otherwise modified by the skilled artisan in formulating the antiperspirant and deodorant embodiments of the present inventions. For solid antiperspirant embodiments, such methods include those described in U.S. Pat. No. 4,822,603 (Farris et al.) and U.S. Pat No. 4,985,238 (Tanner et al.). For pressurized antiperspirant embodiments, such methods include those described in U.S. Pat. 6,136,303 (Ruebusch et al.); U.S. Pat. No. 4,904,463 (Johnson et al.) and U.S. Pat. No. 4,840,786 (Johnson et al.) For soft solid or cream embodiments, such methods are described in U.S. Pat. No. 5,902,571 (Putman et al.) and U.S. Pat. No. 5,902,570 (Bretzler et al.). All such method descriptions in the above-identified patent publications are incorporated herein by reference.

Other methods of making the topical leave-on compositions of the present invention, including the antiperspirant and deodorant embodiments thereof, are described hereinafter for the some of the exemplified compositions of the present invention.

Method of Use

The topical leave-on compositions of the present invention may be applied topically to the desired area of the skin to provide a means for applying an acid-stable pantothenic acid derivative to the skin, preferably in combination with a organic acid such as salicylic acid or an antiperspirant active such as an aluminum-containing antiperspirant salt or polymer.

The antiperspirant and deodorant embodiments of the present invention may be applied topically to the axilla or other area of the skin in an amount effective to reduce or prevent perspiration wetness and malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied one to two times daily, preferably once daily, to achieve effective antiperspirant and malodor control.

The antiperspirant and deodorant embodiments of the present invention can also be applied topically to the axilla as noted above, with the additional purpose or intention of providing a method of softening or conditioning the underarm hair, and thus also providing a method of enhancing the ease of shaving such underarm hair. It has been found that these embodiments of the present invention not only condition or soften the underarm hair, but that consumers notice an enhanced ease of shaving when the underarm hair has been so conditioned or softened within about 72 hours, preferably within about 48 hours, of application of the composition to the underarm. In this context, ease of shaving refers to the consumer perception that the underarm hair is cut more easily, with less drag on the hair and skin, during the shaving process.

The antiperspirant and deodorant embodiments of the present invention can be formulated in a variety of product forms and then applied to the axilla or other area of the skin in the manner described herein. Such product forms include solids (e.g., sticks), semi-solids (e.g., lotions, creams, soft solids), or liquids (e.g. aerosols, non-aerosol sprays, roll-ons, porous dome liquids).

Comparative Data

The topical leave-on compositions of the present invention are evaluated to determine the relative acid or hold stability of selected pantothenic acid derivatives as defined herein (e.g., ethyl panthenol, panthenyl triacetate) relative to other pantothenic acid derivatives (e.g., panthenol, calcium pantothenate). In this context, acid or hold stability is found to correlate with the lack of visibly apparent crystal formation within or extending from the sample product or by the lack of any significant off-odor development, over a 24 hours period at an elevated hold temperature of 85° C.

Samples A and H are antiperspirant and deodorant embodiments of the present invention, whereas Samples C and D are comparative examples that do not contain the selected pantothenic acid derivatives as defined herein. Each comprises by weight of the total composition 25.25% aluminum zirconium trichlorohydrate, 60.00% cyclopentsiloxane, 5.00% fully hydrogenated HEAR oil, 1.25% C18-acid triglyceride, 0.50% vitamin E acetate, 5.00% dimethicone 10 cs, and 3.00% of a pantothenic acid derivative.

Each sample composition is formulated with the above-described ingredients and then held at 85° C. as a heated liquid for a 24 hour period and evaluated during that that period of time for any visibly apparent crystal formations within or extending from the formulation, and for any off-odor development. The evaluated product is maintained in the heated liquid state at 85° C. during the evaluation period to assimilate the elevated processing or hold temperatures often associated with the making of such antiperspirant and deodorant products, and to assimilate those conditions that favor acid-degradation of pantothenic acid derivatives as described herein.

The data from the evaluations as set forth in Comparative Data Table below shows that the compositions containing the selected pantothenic acid derivatives as defined herein (e.g., ethyl panthenol, panthenyl triacetate) do not exhibit the undesirable crystal formation during the 24 hour evaluation period and shows little or no off-odor development as compared to the compositions containing the other pantothenic acid derivatives (e.g., calcium pantothenate, panthenol).

Comparative Data

| Sample | Pantothenic acid derivative | Visible crystal formation | Off-odor formation |
| --- | --- | --- | --- |
| A | Ethyl panthenol | None at 24 hr | Slight at 24 hr |
| B | Panthenyl triacetate | None at 24 hr | None at 24 hr |
| C | Calcium pantothenate | 16 hr | 4 hr |
| D | Panthenol | 18 hr | 4 hr |

EXAMPLES

The following non-limiting examples illustrate specific embodiments of the topical leave-on compositions of the present invention, including the antiperspirant and deodorant embodiments thereof. Also described are methods of manufacture and use directed to the topical leave-on compositions of the present invention. Each of the exemplified compositions is applied topically to the desired area of the skin to provide the desired product or active delivery, including topical delivery of an acid-stable pantothenic acid derivative. The pantothenic acid derivatives in each of the compositions remain stable over prolonged periods of time, e.g., at 1, 3, and 9 months, with no visible sign of undesirable crystal formation and off-odor development. All exemplified amounts are weight percentages based upon the total weight of the antiperspirant stick composition, unless otherwise specified.

In the antiperspirant and antiperspirant examples, each composition is applied topically to the axilla area of the skin, in accordance with the methods of use described herein. Each of the applied compositions are mild and soothing to the skin, especially when applied to irritated skin. Each of the compositions softens or conditions the underarm hair, and enhances ease of shaving.

Example 1

The compositions described in Table 1 are prepared by methods well known in the antiperspirant and deodorant arts for formulating soft solids or creams. Such methods are described in U.S. Pat. No. 5,902,571 (Putman et al.) and U.S. Pat. No. 5,902,570 (Bretzler et al.), which methods are incorporated herein by reference.

TABLE 1

Antiperspirant Soft Solids/Creams

| Ingredients | Example 1.1 | Example 1.2 | Example 1.3 | Example 1.4 |
| --- | --- | --- | --- | --- |
| Al Zr trichlorohydrex glycinate (solid) | 25.25 | 25.25 | 25.25 | 25.25 |
| Dimethicone (10 cs) | 5.00 | 5.00 | 5.00 | 5.00 |
| Fully hydrogenated high erucic acid rapeseed oil (HEAR oil)[1] | 5.00 | 5.00 | 5.00 | 5.00 |
| C18–36 acid triglyceride syncrowax HGLC[2] | 1.25 | 1.25 | 1.25 | 1.25 |
| Perfume | 0.75 | 0.75 | 0.75 | 0.75 |
| Ethyl panthenol | 0.50 | 0.50 | 3.50 | 1.00 |
| Tocopherol acetate | 0.50 | 0 | 0 | 0 |
| Cyclopentasiloxane | QS | QS | QS | QS |

[1]CanAmera, Canada
[2]Croda Inc., New York, New York, USA

Example 2

The compositions described in Table 2 are prepared by methods well known in the antiperspirant and deodorant arts for formulating solid wax stick products. Such methods are in U.S. Pat. No. 4,822,603 (Farris et al.) and U.S. Pat. No. 4,985,238 (Tanner et al.), which methods are incorporated herein by reference.

TABLE 2

Antiperspirant and Deodorant Solid Wax Sticks

| Ingredients | Example 2.1 | Example 2.2 | Example 2.3 | Example 2.4 |
| --- | --- | --- | --- | --- |
| Al Zr trichtorohydrex glycinate (solid) | 20.00 | 20.00 | 20.00 | 20.00 |
| Stearyl alcohol | 11.00 | 11.00 | 11.00 | 11.00 |
| Talc, USP Grade | 6.50 | 7.00 | 7.50 | 3.00 |
| Dimethicone (50 cs) | 3.00 | 5.00 | 5.00 | 5.00 |
| Castor wax | 2.90 | 5.00 | 5.00 | 5.00 |
| Ethyl panthenol | 0.50 | 0.50 | 3.50 | 1.00 |
| Tocopherol acetate | 0.50 | 0 | 0 | 0 |
| Fumed silica | 0.18 | 0.18 | 0.18 | 0.18 |
| Dipropylene glycol | 0.18 | 0.18 | 0.18 | 0.18 |
| Microthene[1] | 0.18 | 0.18 | 0.18 | 0.18 |
| Behenyl alcohol | 0.08 | 0.08 | 0.08 | 0.08 |
| Perfume | 0.75 | 0.75 | 0.75 | 0.75 |
| Cyclopentasiloxane | QS | QS | QS | QS |

[1]Polyethylene beads; Quantum Chem. Corp./USI Div., Cincinnati, Ohio USA

Example 3

The compositions described in Table 2 are prepared by methods well known in the antiperspirant and deodorant arts for formulating solid stick products. Such methods are in U.S. Pat. No. 4,822,603 (Farris et at.) and U.S. Pat. No. 4,985,238 (Tanner et al.), which methods are incorporated herein by reference.

TABLE 3

Antiperspirant and Deodorant Low Residue Solid Sticks

| Ingredients | Example 3.1 | Example 3.2 | Example 3.3 | Example 3.4 |
| --- | --- | --- | --- | --- |
| Al Zr trichlorohydrex glycinate (solid) | 25.25 | 20.00 | 20.00 | 20.00 |

TABLE 3-continued

Antiperspirant and Deodorant Low Residue Solid Sticks

| Ingredients | Example 3.1 | Example 3.2 | Example 3.3 | Example 3.4 |
|---|---|---|---|---|
| Dimethicone (50 cs) | 5.00 | 5.00 | 5.00 | 5.00 |
| Fully hydrogenated high erucic acid rapeseed oil (HEAR oil)[1] | 15.00 | 15.00 | 15.00 | 15.00 |
| Isopar M[2] | 10.00 | 10.00 | 10.00 | 10.00 |
| C-18–36 acid triglyceride syncrowax HGLC[3] | 3.75 | 3.75 | 3.75 | 3.75 |
| Perfume | 0.75 | 0.75 | 0.75 | 0.75 |
| Ethyl panthenol | 0.50 | 0.50 | 3.50 | 1.00 |
| Tocopherol acetate | 0.50 | 0 | 0 | 0 |
| Cyclopentasiloxane | QS | QS | QS | QS |

[1]CanAmera, Canada
[2]C13–14 Isoparaffin; Exxon Chemical Company, Baytown, Texas, USA
[3]Croda Inc., New York, New York, USA

Example 4

The pressurized antiperspirant and deodorant compositions described in Table 4 are prepared by methods well known in the antiperspirant and deodorant art for making pressurized antiperspirant products. Such methods described in U.S. Pat. No. 6,136,303 (Ruebusch et al.); U.S. Pat. No. 4,904,463 (Johnson et al.) and U.S. Pat. No. 4,840,786 (Johnson et al.), which descriptions are incorporated herein by reference.

TABLE 4

Pressurized Antiperspirant and Deodorant Liquids

| Ingredients | Example 4.1 | Example 4.2 | Example 4.3 | Example 4.4 |
|---|---|---|---|---|
| Aluminum chlorohydrate solids | 10.50 | 10.50 | 11.00 | 10.50 |
| SE76 Silicone Gum[1] | 5.00 | 5.00 | 5.00 | 5.00 |
| SWS 801[2] | 15.00 | 15.00 | 15.00 | 15.00 |
| Cyclopentasiloxane | 3.40 | 3.40 | 3.40 | 3.40 |
| Ethyl panthenol | 0.50 | 0.50 | 1.00 | 0.50 |
| Tocopherol acetate | 0.50 | 0 | 0 | 0.50 |
| Propellant A-46[3] | QS | QS | QS | QS |

[1]Silicone gum pre-mix (15% silicone-15 × 10$^6$ cp and 85% cylomethicone); General Electric Company
[2]Diamino-functional silicone, m.w. 76,000; SWS Silicone, Inc.
[3]87/13 isobutene/propane blend

Example 5

The antiperspirant and deodorant liquid compositions described in Table 5 are prepared by methods well known in the antiperspirant and deodorant art for making liquid antiperspirant and deodorant products for roll-on application. Such methods are described in U.S. Pat. No. 4,552,753 (Elm et al.), which descriptions are incorporated herein by reference.

TABLE 5

Antiperspirant and Deodorant Roll-on Liquids

| Ingredients | Example 5.1 | Example 5.2 | Example 5.3 | Example 5.4 |
|---|---|---|---|---|
| Al Zr trichlorohydrex glycinate (solid) | 21.25 | 21.25 | 21.75 | 20.00 |
| Dimethicone (10 cs) | 10.00 | 10.00 | 10.00 | 10.00 |
| Microthene[1] | 7.00 | 7.00 | 7.00 | 7.00 |
| Bentone 38[2] | 1.00 | 1.00 | 1.00 | 1.00 |
| Fumed silica | 0.70 | 0.70 | 0.70 | 0.70 |
| Propylene carbonate | 0.30 | 0.30 | 0.30 | 0.30 |
| Perfume | 0.50 | 0.50 | 0.50 | 0.50 |
| Ethyl panthenol | 0.50 | 0.50 | 3.50 | 1.0 |
| Tocopherol acetate | 0.50 | 0 | 0 | 0 |
| Cyclopentasiloxane | QS | QS | QS | QS |

[1]Polyethylene beads; Quantum Chem. Corp./USI Div., Cincinnati, Ohio USA
[2]Rheox Inc., Hightstown, New Jersey, USA

Example 6

The composition described in Table 6 is a topical leave-on composition in the form of oil-in-water emulsion that is prepared by combining the listed ingredients using conventional mixing and formulating techniques as described below.

Initially, a water phase is prepared by heating water to 82° C. and then adding the selected pantothenic acid derivative to the heated water and maintaining the water at between 65–75° C. An oil phase is then prepared in a separate vessel by heating and mixing together the cetyl alcohol, stearyl alcohol, steareth-21, dimethicone, and cyclopentasiloxane, at a temperature of from 65–75° C. A salicylic acid phase is then prepared in yet another vessel by heating and mixing together the salicylic acid and PPG-14 butyl ether at a temperature of from 65–75° C. The salicylic acid phase is then combined with the oil phase at a temperature of from 65–75° C., and then the resulting combination is mixed together with the water phase and milled at a temperature of from 65–75° C. The milled combination is then cooled to between 40–50° C. before adding to it the disodium EDTA and any other remaining or minor ingredients. The resulting composition has a pH of from 3.0 to 4.5, or is otherwise modified to have a an adjusted pH of from 3.0 to 4.5.

TABLE 6

Low pH Skin Care Cream

| Ingredients | Example 6.1 |
|---|---|
| Salicylic acid | 2.0 |
| PPG-14 butyl ether | 8.0 |
| Glycerin | 4.0 |
| Stearyl alcohol | 1.5 |
| Cetyl alcohol | 3.0 |
| Distearyl dimethyl ammonium chloride | 0.10 |
| d-Ethyl panthenol | 3.0 |
| Propylene glycol | 3.0 |
| Steareth-21 | 2.0 |
| Steareth-2 | 1.0 |
| Dimethicone 50 cs | 1.0 |
| Cyclopentasiloxane | 1.0 |
| Disodium EDTA | 0.02 |
| Water | QS 100 |

Example 7

The composition described in Table 7 is prepared by mixing together under ambient conditions the oil phase ingredients, and then mixing together in a separate vessel all of the water phase ingredients. The water phase is then slowly added to the oil phase over a period of about 50 minutes while mixing at 190 rpm with an IKA overhead mixer with a twin turbin blade. The resulting composition is then subjected to further mixing for an additional 15 minutes, before being milled using an IKA T25 mill for 20–30 seconds at high speed. The resulting milled product is then mixed by hand for an additional 20–30 seconds using a spatula, and then packaged in a suitable dispenser for topical leave-on application to the skin.

TABLE 7

Clear Gel Antiperspirant and Deodorants

|  | Example 7.1 |
|---|---|
| Water Phase | |
| Water | QS |
| Aluminum chlorohydrate solution[1] | 30 |
| Ethanol | 10 |
| d-Ethyl panthenol | 3.0 |
| Propylene glycol | 1.0 |
| Oil Phase | |
| Dimethicone 50 cs | 9.030 |
| Cyclomethicone dimethicone copolyol | 9.350 |

[1]Aqueous solution containing 50% active

Example 8

The topical wipes described in Table 8 are prepared by methods well known in the personal care and substrate art for making topical wipes comprising an aqueous liquid. Such methods are described in U.S. Ser. No. 09/624,320 (Pung et al.), filed Jul. 24, 2000, which it descriptions are incorporated herein by reference.

All exemplified amounts described in Table 8 are weight percentages based upon the total weight of the aqueous liquid component, unless otherwise specified. Each exemplified composition is coated onto a 12 count stack of 68 gsm (gram/m$^2$) fluid-entangled, nonwoven, flexible substrates (70%Rayon, 30%PET). Each of the topical wipe products described in Table 8 is applied topically to the face, forearms, and neck, to provide the desired active application to the skin.

TABLE 8

Topical Wipes

| Aqueous liquid Ingredients | Example 8.1 | Example 8.2 | Example 8.3 | Example 8.4 |
|---|---|---|---|---|
| Ethanol | 10.00 | 10.00 | 10.00 | 10.00 |
| Propylene glycol | 0.50 | 0.50 | 0.50 | 0.50 |
| Sodium benzoate | 0.02 | 0.02 | 0.02 | 0.02 |
| Tetrasodium EDTA | 0.01 | 0.01 | 0.01 | 0.01 |
| Perfume | 0.02 | 0.02 | 0.02 | 0.02 |
| Salicylic acid | 1.0 | 0.5 | 0.25 | 0.5 |
| d-Ethyl panthenol | 1.0 | 0 | 0.25 | 0.25 |
| d-Panthenyl triacetate | 0 | 0.5 | 0 | 0.25 |
| Deodorant Perfume | 0.01 | 0.01 | 0.01 | 0.01 |
| Water | QS | QS | QS | QS |

What is claimed is:

1. Antiperspirant and deodorant compositions comprising:
    (a) from about 0.1% to about 30% by weight of an aluminum-containing antiperspirant active;
    (b) from about 0.01% to about 10% by weight of a pantothenic acid derivative having the formula:

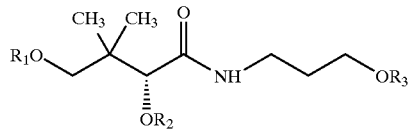

wherein $R_1$, $R_2$ and $R_3$ are independently selected from the group consisting of hydrogen, C2–C20 hydrocarbons, C2–C20 carboxylic acid esters, and combinations thereof, and wherein not more than two of $R_1$, $R_2$ and $R_3$ are hydrogen;
    (c) from about 10% to about 99.89% by weight of a liquid carrier;
    (d) wherein said composition is stable after 24 hours at 85 C., wherein stable means that said composition is substantially free of off-odor and free of undesirable visible crystals; and
    (e) wherein said pantothenic acid derivative is stable in the presence of said aluminum-containing antiperspirant active.

2. The composition of claim 1, wherein $R_1$, $R_2$ and $R_3$ are independently selected from the group consisting of hydrogen, C2–C8 hydrocarbons, C2–C8 carboxylic acid esters, and combinations thereof.

3. The composition of claim 2, wherein $R_1$ and $R_2$ are hydrogen, and $R_3$ is a C2–C8 hydrocarbon, C2–C8 carboxylic acid ester, or combinations thereof.

4. The composition of claim 3, wherein $R_1$ and $R_2$ are hydrogen and $R_3$ is ethyl.

5. The composition of claim 1, wherein the pantothenic acid derivative represents from about 0.05% to about 5%, by weight of the composition.

6. The composition of claim 1, wherein the underarm active is an antiperspirant active selected from the group consisting of zirconium-containing active, aluminum-containing active, and combinations thereof, and represents from about 5% to about 30% by weight of the composition.

7. The composition of claim 6, wherein the antiperspirant active is selected from the group consisting of aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

8. The composition of claim 1, wherein the liquid carrier comprises a cyclomethicone liquid that represents from about 5% to about 80% by weight of the composition.

9. The composition of claim 8, wherein the liquid carrier further comprises a non-volatile silicone that represents from about 1% to about 35% by weight of the composition.

10. The composition of claim 1, wherein the composition further comprises from about 0.1% to about 30% by weight of a suspending agent.

11. The composition of claim 1, wherein the composition is in the form of a solid stick.

12. The composition of claim 1, wherein the composition is in semi-solid form.

13. The composition of claim 1, wherein the composition is in the form of a pressurized liquid.

14. Topical leave-on compositions comprising:
(a) from about 0.01% to about 10% by weight of a pantothenic acid derivative having the formula:

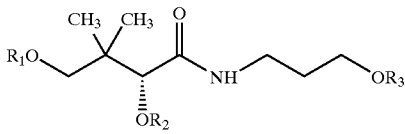

wherein $R_1$, $R_2$ and $R_3$ are independently selected from the group consisting of hydrogen, C2–C20 hydrocarbons, C2–C20 carboxylic acid esters, and combinations thereof, and wherein not more than two of $R_1$, $R_2$ and $R_3$ are hydrogen;
(b) from about 10% to about 99.99% by weight of an aqueous carrier, wherein the topical leave-on compositions have a pH of from about 2.0 to about 5.0 and are intended solely for leave-on application;
(c) wherein said composition is stable after 24 hours at 85 C., wherein stable means that said composition is substantially free of off-odor and free of undesirable visible crystals; and
(d) wherein said pantothenic acid derivative is stable in the presence of said aluminum-containing antiperspirant active.

15. The topical leave-on composition of claim 14, wherein the composition is substantially free of cleansing surfactants.

16. The topical leave-on composition of claim 15, wherein the composition contains less than 1% by weight of a cleansing surfactant.

17. The topical leave-on composition of claim 14, wherein $R_1$, $R_2$ and $R_3$ are independently selected from the group consisting of hydrogen, C2–C8 hydrocarbons, C2–C8 carboxylic acid esters, and combinations thereof.

18. The composition of claim 17, wherein $R_1$ and $R_2$ are hydrogen, and $R_3$ is a C2–C8 hydrocarbon, C2–C8 carboxylic acid ester, or combinations thereof, and wherein the pantothenic acid derivative is in the d-isomeric form.

19. The composition of claim 18, wherein $R_1$ and $R_2$ are hydrogen and $R_3$ is ethyl.

20. The composition of claim 14, wherein the pantothenic acid derivative represents from about 0.05% to about 5%, by weight of the composition.

21. The composition of claim 14, wherein the carrier comprises a cyclomethicone liquid that represents from about 5% to about 80% by weight of the composition.

22. The composition of claim 14, wherein the composition further comprises from about 0.1% to about 30% by weight of a suspending agent.

23. The composition of claim 14, wherein the composition further comprises from about 0.1% to about 20% by weight of an organic acid.

24. The composition of claim 23, wherein the organic acid comprises salicylic acid.

25. The composition of claim 23, wherein the organic acid comprises an aluminum-containing antiperspirant active.

26. The composition of claim 14, wherein said composition further comprises a topical substrate on or within which said composition is coated or treated.

27. The composition of claim 26, wherein the topical substrate is a water-insoluble, non-woven substrate.

28. A method of controlling underarm perspiration wetness and odor, said method comprising the topical leave-on application to the underarm of from about 0.1 grams to about 20 grams per underarm of a composition according to claim 14.

29. A method of controlling underarm perspiration wetness and odor, said method comprising the topical leave-on application to the underarm of from about 0.1 grams to about 20 grams per underarm of a composition according to claim 1.

30. A method of enhancing ease of shaving underarm hair, said method comprising applying to the underarm from about 0.1 grams to about 20 grams of a composition according to claim 1, and the shaving of the underarm within 72 hours of said topical application.

31. A method of conditioning or softening underarm hair, said method comprising applying to the underarm from about 0.1 grams to about 20 grams of a composition according to claim 1.

* * * * *